(12) United States Patent
Kozulic (10) Patent No.: US 7,025,864 B2
(45) Date of Patent: Apr. 11, 2006

(54) METHOD AND APPARATUS FOR RECOVERING TARGET MOLECULES FROM A GEL CONTAINING SAID TARGET MOLECULES

(75) Inventor: Branko Kozulic, Zurich (CH)

(73) Assignee: Elchrom Scientific A.G., Zurich (CH)

( * ) Notice: Subject to any disclaimer, the term of this patent is extended or adjusted under 35 U.S.C. 154(b) by 524 days.

(21) Appl. No.: 10/383,683

(22) Filed: Mar. 10, 2003

(65) Prior Publication Data

US 2004/0178073 A1     Sep. 16, 2004

(51) Int. Cl.
  *G01N 27/447*  (2006.01)
  *G01N 27/453*  (2006.01)

(52) U.S. Cl. .................... 204/462; 204/613
(58) Field of Classification Search ........ 204/601–621, 204/462–465, 627
See application file for complete search history.

(56) References Cited

U.S. PATENT DOCUMENTS

| | | | |
|---|---|---|---|
| 3,719,580 A | 3/1973 | Roberts et al. | |
| 3,888,758 A | 6/1975 | Saeed | |
| 3,989,612 A | 11/1976 | Kragt et al. | |
| 4,545,888 A | 10/1985 | Walsh | |
| 4,576,702 A | 3/1986 | Peck et al. | |
| 4,576,703 A | 3/1986 | Peck et al. | |
| 4,608,147 A | 8/1986 | Clad | |
| 4,725,348 A | 2/1988 | Diekmann | |
| 4,747,918 A | 5/1988 | Wassenberg, II | |
| 4,877,510 A | 10/1989 | Chen | |
| 4,964,961 A | 10/1990 | Brautigam et al. | |
| 5,102,518 A | 4/1992 | Doering et al. | |
| 5,185,466 A | 2/1993 | Kozulic et al. | |
| 5,202,007 A | 4/1993 | Kozulic | |
| 5,259,943 A | 11/1993 | Kozulic et al. | |
| 5,284,559 A | 2/1994 | Lim et al. | |
| 5,340,449 A | 8/1994 | Shukla | |
| 5,384,022 A | 1/1995 | Rajasekaran | |
| 5,439,573 A | 8/1995 | Lao | |
| 5,527,680 A | 6/1996 | Tran et al. | |
| 5,541,255 A | 7/1996 | Kozulic | |
| 5,840,877 A | 11/1998 | Kozulic | |
| 6,198,107 B1 | 3/2001 | Seville | |
| 6,451,192 B1 | 9/2002 | Ooike et al. | |

*Primary Examiner*—Nam Nguyen
*Assistant Examiner*—Anthony Fick
(74) *Attorney, Agent, or Firm*—Michael G. Gilman (57) ABSTRACT

A preparative electrophoresis apparatus suitable for recovery of molecules from gels comprises two spaced apart electrode compartments connected by a conduit that descends from the bottom of the electrode compartments in a V-shaped or U-shaped form. The conduit serves as a reservoir for collecting electroeluted molecules. Two electrophoresis buffers are used, a first one of a low concentration and density, and a second one of a high concentration and density. The electrode compartments are filled with the first electrophoresis buffer solution while the conduit is filled with the second electrophoresis buffer solution. Under the influence of an electric field, the molecules exit the gel and concentrate in the high concentration buffer. After a certain time, usually a time that is sufficient for driving substantially all desired molecules out of the gel, the electric field is switched off. The high concentration buffer containing the electroeluted molecules is withdrawn from the conduit. The target molecules may be recovered from the high concentration buffer solution.

22 Claims, 6 Drawing Sheets

METHOD AND APPARATUS FOR RECOVERING TARGET MOLECULES FROM A GEL CONTAINING SAID TARGET MOLECULES

BACKGROUND OF THE INVENTION

1. Field of the Invention

Electrophoresis is a separation method based on different migration rates of dissolved ions in an electric field. When the ions migrate through a gel, the chemical and physical properties of the gel influence migration rates of various ions to varying degrees. Therefore, gel electrophoresis provides a higher resolving power than free solution electrophoresis. A gel also reduces diffusion of separated zones after the electric field has been switched off, facilitating the detection of the zones. Gels of different chemical compositions, physical properties and shapes have been used for electrophoresis, in a variety of different apparatuses, for separating ions as small as nucleotides or as large as chromosomal DNA. In general, there are two types of gel electrophoresis: analytical and preparative. In analytical electrophoresis, the gel is discarded after the detection of separated zones. In preparative gel electrophoresis, after the detection of a target molecule, a gel piece containing the zone of interest (that is the zone containing the target molecules) is further processed to recover the ions from the gel zone. This invention relates to an apparatus and method for preparative electrophoresis, and especially an apparatus for recovering target molecules from a gel that has undergone electrophoresis.

2. Description of Prior Art

Gel electrophoresis is particularly well suited for the separation of biological macromolecules, such as proteins, nucleic acids and charged polysaccharides. Recovery of the separated macromolecules is often needed in many research applications. In industry, gel electrophoresis is routinely used, for example, for the preparation of high purity oligonucleotides (oligos), especially those longer than about 50 base pairs. Currently, no other method can match the degree of purity of product achieved by gel electrophoresis.

Preparative gel electrophoresis can be carried out in a continuous or discontinuous mode. In continuous mode, the separated zones are collected in the order they emerge from the gel. For example, Hjerten et al. (Analytical Biochemistry, 1969, 27:108–129) describe an apparatus in which protein molecules leaving a polyacrylamide gel enter a bed of agarose particles from which they are eluted using a stream of buffer leading to detector and fraction collector. Alternatively, a semipermeable membrane can be placed near the gel end to prevent dilution of the electroeluting molecules in an electrophoresis buffer, as described for example in U.S. Pat. Nos. 5,284,559, 3,888,758 and 3,719,580.

In a discontinuous mode, the separated zones are made visible, or their position can be determined by other means, for example by comparison to markers. Then the gel part of interest is cut out using a suitable means such as a nylon string, needle, scalpel or razor blade. Different methods have been used for recovering the target molecules present inside the cut gel piece, including crushing the gel into small particles followed by incubation to let the desired molecules diffuse out of the gel. Electroelution recovery of target molecules from gel is the preferred method because it is faster and provides higher recovery yields than other methods. The molecules that are electrophoretically driven out of the gel need to be stopped from migrating far into the electrophoresis buffer, as otherwise their concentration would decrease to unacceptably low levels. Many solutions that prevent excessive dilution have been disclosed. For example, U.S. Pat. No. 4,545,888 discloses the use of DEAE paper to adsorb nucleic acids that migrate out of the gel. The use of semipermeable membranes, arranged in different ways, is disclosed for example in U.S. Pat. Nos. 5,527,680, 5,439,573, 5,384,022, 5,340,449, 5,102,518, 4,964,961, 4,877,510 and 4,608,147. The disadvantage of the membranes is that they tend to adsorb electroeluted molecules, reducing the yield. To improve the recovery yield, it is necessary to temporarily change polarity of the electric field in order to release the molecules from the membrane. Another disadvantage is that some molecules denature in contact with a membrane, as pointed out by Hjerten et al. (Analytical Biochemistry, 1969, 27:108–129).

When electroeluting fast migrating molecules from low percentage gels, like DNA from agarose gel, then a brief application of the electric field in a small buffer volume may be adequate (U.S. Pat. No. 4,747,918 to Wassenberg). However, this procedure will not work with the molecules characterized by low migration rates or with high percentage gels. In order to slow down the electroeluted molecules, one can increase the ionic strength of the buffer into which the molecules migrate after leaving the gel. It is well known to those skilled in the art that migration rate of a molecule is reduced when it enters a buffer of high conductivity (concentration). Thus Kragt et al. in U.S. Pat. No. 3,989,612 added sodium chloride to phosphate buffer on one side of their electroelution cassette in which the gel makes a leak proof seal with other parts of the cassette.

In U.S. Pat. Nos. 4,576,702 and 4,576,703 Peck et al. disclose the use of a salt solution pipetted into a reservoir that receives electroeluted molecules. A similar disclosure can be found in U.S. Pat. No. 4,725,348 to Diekmann. In the apparatuses of both Peck et al. and Diekmann, electrode compartments are separated by a block (Diekmann), or a bridge (Peck et al.), that ascends from the bottom of the electrode compartments. The V-shaped reservoir, that contains a salt solution and receives the electroeluted molecules, is constructed in the block (bridge) in such a way that it connects the two electrode compartments. The two electrode compartments communicate also through at least one additional conduit that needs to be closed during electroelution. Prior to removal of the salt solution containing the electroeluted molecules, it is necessary to open other conduits in order to lower the level of electrophoresis buffer below the level of the openings of the V-shaped reservoir. For this purpose, the apparatuses of Peck et al. and Diekmann contain valves that need to be closed and opened in a defined manner, making the operation complicated. In addition, the need for valves inside the apparatus makes the construction of their apparatuses complex and expensive.

Now it has been found that the apparatus of present invention can overcome the above drawbacks of the apparatuses disclosed in prior art because it is simplified and is effective.

SUMMARY OF THE INVENTION

An apparatus for preparative electrophoresis and recovery of target molecules of present invention comprises two electrode compartments connected by a conduit that is disposed below the bottom of the electrode compartments. In a preferred form of this invention, the conduit has a regular V-shaped or U-shaped form. However, the regularity of the conduit is not a necessary feature of this invention. Two electrophoresis buffers are used, a first one of a lower ion concentration and density, and a second one of a higher ion concentration and density. The conduit serves as a reservoir for collecting target molecules that have been electroeluted out of a gel sample that is disposed in the first buffer solution. The conduit preferably has an opening at its bottom through which, first it is possible to fill the conduit with a high concentration, second buffer solution; and later to withdraw the buffer containing electroeluted molecules. In one way of operation, a syringe, or the like, filled with the second, high concentration, buffer is attached to the opening at the bottom of the conduit. The two compartments are filled with a first electrophoresis buffer of low concentration. A gel piece containing the molecules of interest is positioned at the bottom of an electrode compartment adjacent to a confluence between one opening of the conduit and one electrode compartment. By pushing the piston of the syringe, the conduit is filled with the high concentration buffer that displaces the low concentration electrophoresis buffer in an upward direction and into the electrode compartment(s). Under the influence of an electric field, the molecules exit the gel and concentrate in the high concentration buffer. After a certain, predetermined, time, sufficient for driving substantially all target molecules out of the gel piece, the electric field is switched off. The high concentration buffer containing the electroeluted target molecules is then withdrawn from the conduit, suitably using the same syringe as was used to inject the high concentration buffer. The target molecules can be recovered from the high concentration buffer solution by known techniques.

DETAILED DESCRIPTION OF THE PREFERRED EMBODIMENTS

Figure 1:
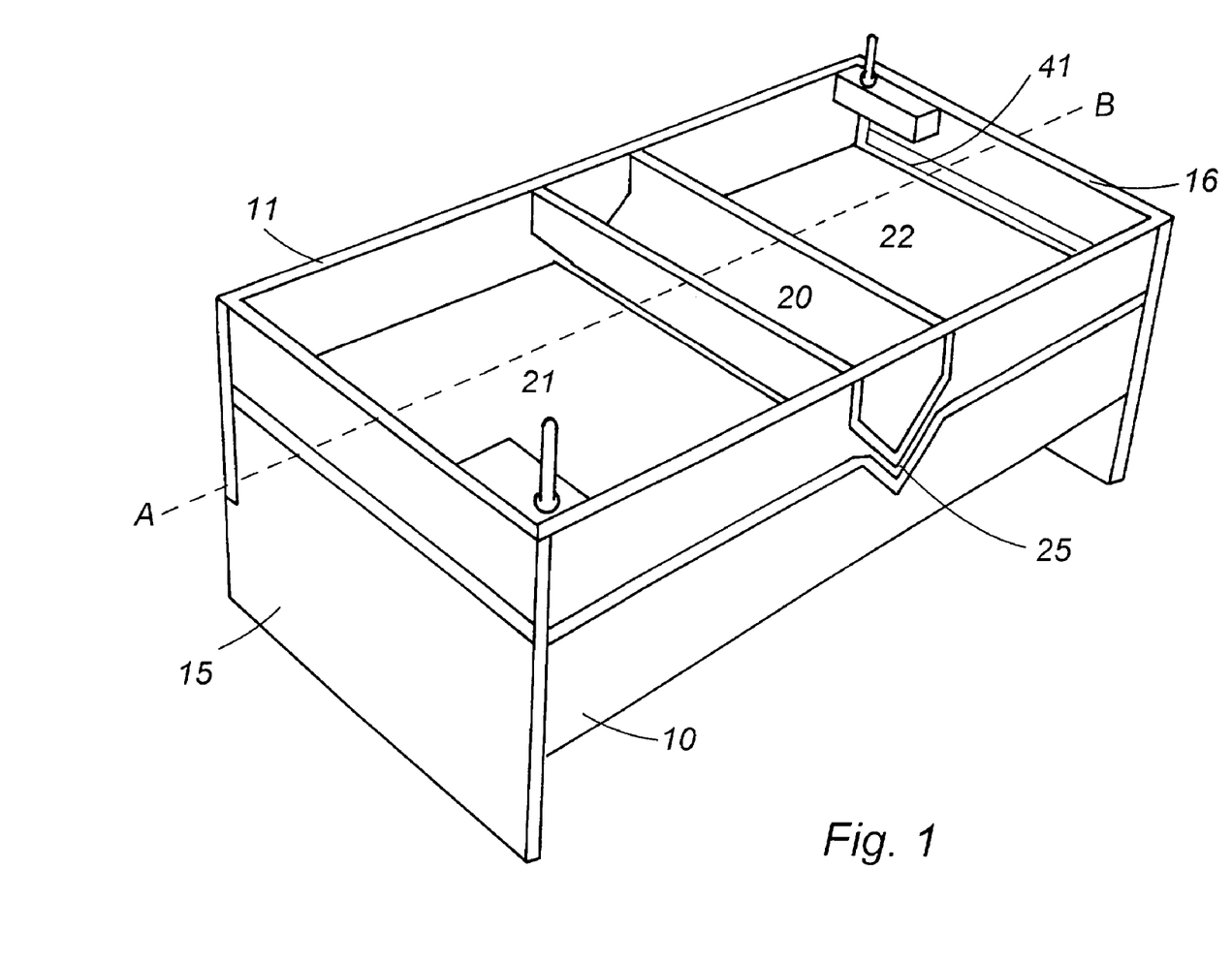
FIG. 1 is a schematic perspective view of an electroelution apparatus illustrating the principles of the invention.
Figure 2:
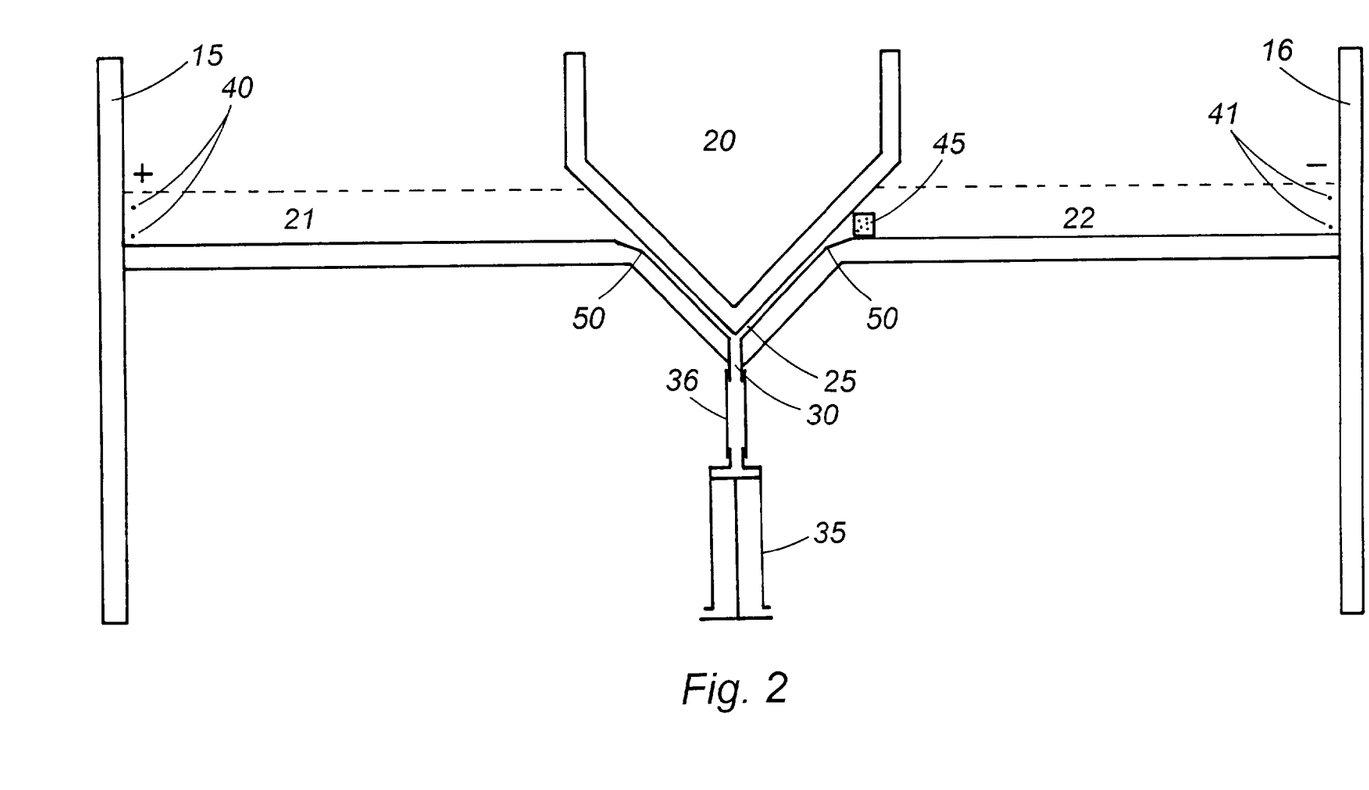
FIG. 2 is a sectional side view of the electroelution apparatus of present invention taken along the line A-B in FIG. 1.

Referring to FIG. 1 and FIG. 2, the apparatus of present invention contains a front wall 10, a rear wall 11 and side walls 15 and 16 which, together with a central block 20, define two liquid tight electrode compartments 21 and 22. The electrode compartments can have a plurality of side walls, suitably in a rectangular shape, or these compartments can have an arcuate side wall, suitably in a conic section shape, such as an ellipse. Rectangular walled electrode compartments are preferred. The electrode compartments adapted to contain first buffer solution communicate with each other through a conduit 25 defined by the space between a depressed portion of the bottom of the buffer compartments and the central block 20 in such a way that the conduit is generally below the level of the bottom of the compartments, suitably in a U or V-shape. The conduit preferably has an opening 30 at its lowest point. A syringe 35 is suitably connected to the opening 30 via a tubing 36.

Each electrode compartment 21 and 22, has an electrode 40 and 41, respectively, preferably positioned at the respective side walls distal from the conduit.

Two electrophoresis buffers, one of a low and another of a high concentration, are used with the apparatus of present invention. The second electrophoresis buffer, that has a high concentration, is drawn into the syringe 35 and then the syringe is attached to the tubing 36. The first electrophoresis buffer, that has a low concentration, is poured into the apparatus such that it fills both compartments 21 and 22. It is practical to first pour the low concentration, first buffer solution into one of the buffer compartments, whereby also filling the other compartment through the conduit 25. A gel piece 45, containing one or more target molecules to be recovered, is placed at the bottom of one electrode compartment 21 or 22, preferably close to the confluence of the conduit 25 and one of the electrode compartments. Then the piston of the syringe 35 is pushed to fill the conduit 25 with a high concentration buffer. The low concentration buffer, that was initially in the conduit 25, is displaced out of the conduit and into the compartments 21 and 22 because it has a lower density. Electric current is applied by connecting leads, that can be adapted to pass through a suitable lid that is adapted to cover the compartments, (not shown) from a power supply (not shown) with the electrodes 40 and 41. Direct current electric power is applied through the electrodes for a time period sufficient for driving the target molecules out of the gel and into the conduit. Thereafter, the power is switched off. The piston of the syringe 35 is pulled to withdraw the high concentration buffer, containing the eluted molecules, from the conduit.

The syringe 35 containing the electroeluted molecules is disconnected from the tubing 36, whereupon, the first electrophoresis buffer can be drained from the apparatus through the opening of the conduit left by removing the syringe 35. The apparatus can then be rinsed, suitably with deionized water, to prepare it for the next usage. The electroeluted molecules may be separated from the high concentration buffer and processed further by conventional means if desired.

Of course, it is within the scope of this invention to first fill the conduit with the second buffer solution and then fill the electrode compartments with the first buffer solution. It is also within the scope of this invention to place the gel into the first electrophoresis solution after the conduit is filled with the second electrophoresis solutions. However, these are less preferred alternatives.

The apparatus of the present invention is suitably made of a non-conductive material, such as a plastic like polymethylmethacrylate, polycarbonate or a similar material. Its overall size depends on the dimensions of the gel piece that will contain the target molecules to be electroeluted. A typical width of a slab gel used for electrophoresis is from about 6 to 20 cm. When a single sample well is provided across the whole width of the compartments, then the gel piece cut for electroelution will be comparable to the length of the conduit, that is about 6 to 20 cm wide in the illustrated embodiment. The size of the gel is not critical to the practice of this invention. The side walls 15 and 16 are preferably about 1 cm wider than the gel piece. The length of the front and back walls 10 and 11 is selected such that the buffer compartments can accept a buffer volume sufficient for conducting the electroelution. At least one of the front or back walls may be shorter compared to the height of the side walls such that enough space is left between the bench, upon which the apparatus is intended to be disposed, and the opening 30 for easy access to the syringe 35 and tubing 36.

Figure 3:
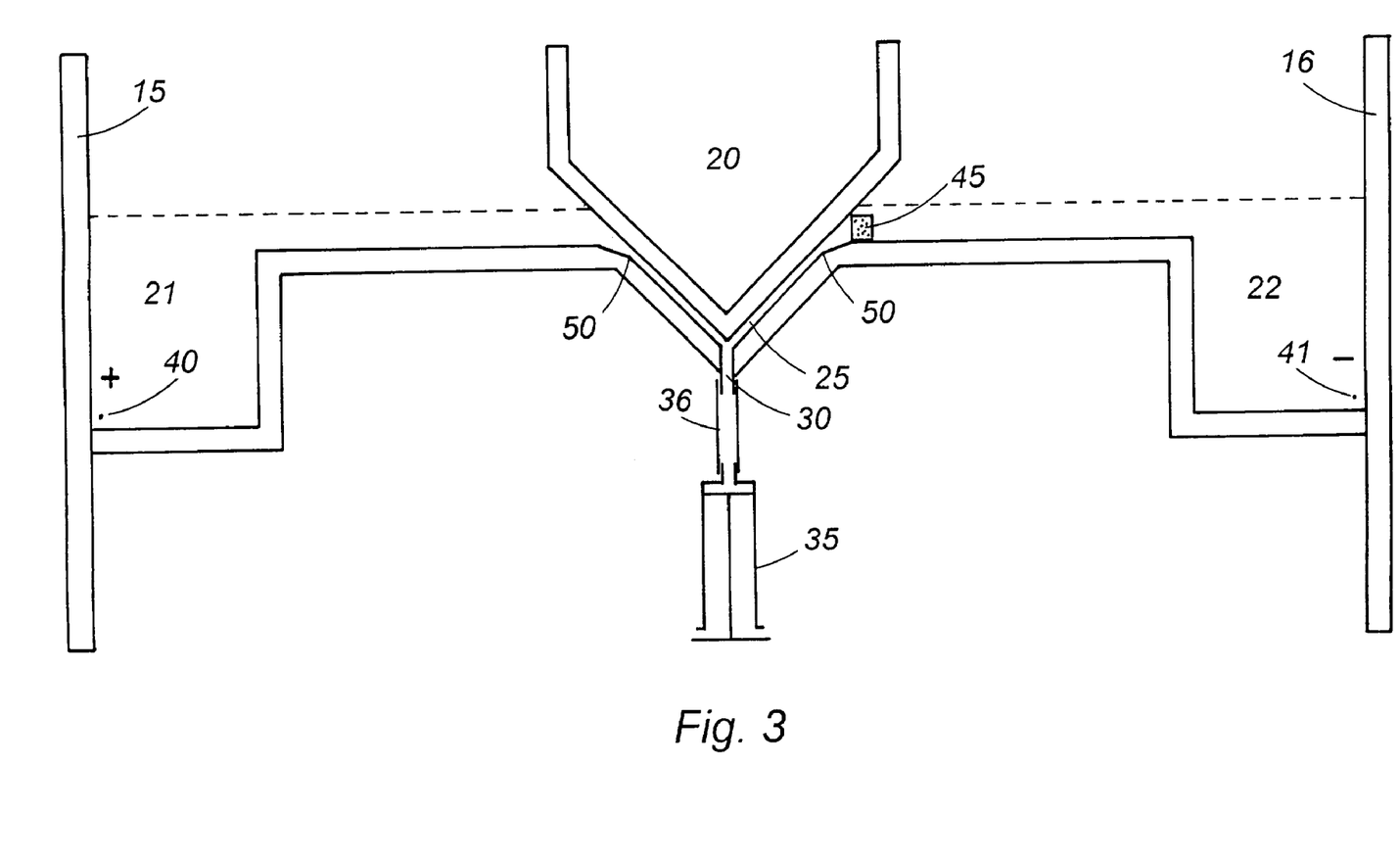
FIG. 3 is a side view of an electroelution apparatus of present invention of another design.

The central block 20 is positioned preferably in the middle of the apparatus. It can be made of a solid piece of plastic, filling the whole space between the two buffer compartments except for the conduit 25. However, it is preferable to have a cavity in the central part of the block 20, as shown in FIGS. 1–3, because this enables better heat dissipation from the conduit 25. Because the conduit contains a buffer of high concentration, the buffer heats up during electroelution and transfers the heat to the surrounding plastic. If the molecules that collect in the conduit are heat sensitive, it may be necessary to keep the temperature of the apparatus low in order to prevent denaturation of the electroeluted molecules. The heat can be controlled by pouring cold water into, or passing cold water through, a cavity in the central block prior to switching on the electric field, and/or while the electric field is in operation. If the cold water is disposed in the cavity only prior to start of the electroelution, the temperature of the buffer will gradually increase during electroelution. Alternatively, a heat exchange element can be placed into that cavity to keep the temperature constant during electroelution. As shown in FIG. 2 and FIG. 3, in the preferred embodiments, the surfaces of the central block 20 that define the conduit 25 extend to a point beyond the top opening of the conduit (that is above the bottom of the buffer compartments 21 and 22). The extensions above the compartment bases may extend at the same or a different angle as the angle of the conduit. These extensions may terminate at a different point relative to the opening of the conduit.

The buffer compartments 21 and 22 are preferably of the same size, but they may also have different dimensions. For example, the conduit can be positioned closer to side wall 15 than to side wall 16. It is within the scope of this invention for the bottom of the buffer compartment 21 to be elevated in comparison to bottom of the buffer compartment 22. Alternatively, both compartments may have bottoms with elevated areas as compared to the depth of the compartments at the respective side walls. The bottoms of both buffer compartments can be substantially flat, except for the conduit, as shown in FIG. 2. Alternatively, the bottom of one, or both, compartments can have a deeper area close to the electrodes, as shown in FIG. 3. The choice depends upon the desired buffer capacity of the compartments, which in turn depends on the expected duration of electroelution. It takes longer to elute a large molecule from a high concentration gel than from a low concentration gel, as known to those skilled in the art. Another consideration is the linearity of the electric field, which is better in the design shown in FIG. 2 than in the design shown in FIG. 3. The position of the electrodes and the shape of the buffer compartment influence the linearity of the electric field, as disclosed in U.S. Pat. No. 5,259,943, which is incorporated herein by reference. It is within the scope of this invention for the apparatus to have one electrode compartment for housing the low concentration buffer solution and a conduit as described herein without the necessity of having a second electrode compartment, but this is not preferred. In such a structure, one electrode means would be disposed in the electrode compartment housing the lower concentration buffer solution, and the other electrode means would be disposed in effective contact with the high concentration buffer solution in the conduit, suitably at the distal end of the conduit relative to the electrode compartment.

The conduit 25 is preferably of V-shape. Other shapes are possible, and a U-shaped conduit is also adequate. It is important that the shape of the conduit is such that filling it with a second buffer of high conductivity can be done by displacing a first buffer of low conductivity without significant mixing of the two buffers. Size of the conduit will vary in dependence on the desired volume of the second buffer it needs to receive. On the one hand, it is important to keep the buffer volume low in order to avoid excessive dilution of the electroeluted molecules. On the other hand, it is important that the volume of the second, high conductivity, buffer be sufficiently large to keep the electroeluted molecules in the conduit. If the buffer volume is too low, then some electroeluted molecules will exit the conduit before the remaining molecules are driven out of the gel. It is convenient to have the width of the conduit between about 0.5 mm and 3 mm, with the preferred width of about 1 mm. When the side walls 15 and 16 are 10–15 cm wide, then the preferred volume of the conduit is about 5 ml. When the conduit is V-shaped, then the preferred angle under which it descends is about 45°. Other angles can be used. The conduit may have the same or different width over its cross-section. It was found to be beneficial to increase the width at the top of the conduit at the confluence of the electrode compartment(s) and the conduit, as shown at the position marked 50 in FIG. 2 and FIG. 3. This helps to avoid spilling of the high conductivity buffer over the bottom of the buffer compartments during filling of the conduit. The conduit is filled with the second buffer preferably up to the position where the opening becomes wider (position 50), but a smaller or larger buffer volume will also work. It is important to avoid overflowing the second buffer from the conduit over the bottom of the buffer compartment close to the gel piece, as this reduces the recovery yield. On the other hand, withdrawing a small volume of the first electrophoresis buffer together with the second electrophoresis buffer containing the molecules of interest usually will not compromise their purity, and may even increase the yield.

The opening 30 at the bottom of the conduit is preferably positioned in the middle of the conduit. The opening can be at another place, for example it can extend from the bottom of the conduit through the front wall 10. When the opening is in the middle, the bottom of the conduit can be tapered towards the middle to facilitate quantitative withdrawal of the high concentration buffer containing the electroeluted target molecules.

The apparatus of present invention can function also without the opening 30. Filling of the conduit and removal of the second buffer from the conduit are then done from above by means of a tubing, or a needle, inserted close to bottom of the conduit. However, this is a less preferred solution, because it is difficult to prevent significant mixing of the two buffers when manually filling the conduit, and also it is more difficult to withdraw the high concentration buffer after completion of the electroelution. The use of an electrically driven pump may avoid the mentioned difficulties.

In the practice of present invention, the level of the first electrophoresis buffer remains higher than the level of the second electrophoresis buffer throughout the operation. In contrast, in the prior art apparatuses of Peck and Diekmann, the level of the low concentration electrophoresis buffer is brought to below the level of the high concentration buffer by opening a valve between the two buffer compartments followed by draining the first electrophoresis buffer. Only after the level of the first buffer has been lowered, is the high concentration buffer, containing the electroeluted molecules, withdrawn. This difference in operation is a consequence of different positioning of the conduit filled with a high concentration buffer in the apparatus of present invention as opposed to the apparatuses of Peck and Diekmann.

The syringe 35 can be directly connected, via the tubing 36, to the opening of the conduit, or the connection may be through a valve. Direct connection is simpler, but the use of a valve may be advantageous in some instances. For example, a three-way valve would avoid immediate draining of the first electrophoresis buffer after disconnecting the syringe. In addition, by switching the valve to a tubing leading to a buffer waste or a sink, the buffer could be drained and the apparatus rinsed before next usage without moving the apparatus. Automated buffer filling and withdrawal would require the use of a valve.

The electrodes 40 and 41 are preferably each made of two wires when the electrode compartments are of the design shown in FIG. 2, as this improves homogeneity of the electric field compared to the electrodes made of only one wire. Additional wires, or electrodes made of a strip, can be used as well. The electrodes are preferably made of a precious metal, such as platinum or its alloys.

The first electrophoresis buffer can comprise any ions known to those skilled in the art to be suitable for an electrophoresis buffer. Generally, the buffer ion concentration will be between about 10 mM and 200 mM, preferably between 20 mM and 60 mM. Its pH will depend on the charge and stability of the molecules to be electroeluted. The choice of the first electrophoresis buffer depends also on the exact composition and concentration of the buffer that was used earlier for electrophoretic separation of the molecules that are being subjected to electroelution. It is desirable that the two buffers be the same or compatible, to avoid the need for buffer equilibration. For example, when nucleic acids are separated in 30 mM Tris-acetate, 0.75 mM EDTA buffer pH 8.1 (TAE buffer), then the same buffer can also be used as the first electrophoresis buffer for electroelution. The optimal level of the first electrophoresis buffer is generally a few millimeters above the gel piece. The apparatus may contain a leveling device and screws for adjusting its horizontal position.

The second electrophoresis buffer can be composed of the same ions as the first electrophoresis buffer, or it may contain different ions. Its concentration will generally be from about 0.2 M to 2 M, preferably from about 0.5 M to 1 M. A salt, for example sodium chloride, can be used to increase ionic strength of the buffer. Because of its higher concentration, the second electrophoresis buffer possesses a higher conductivity compared to the first electrophoresis buffer. Therefore, molecules leaving the gel piece migrate at a lower rate in the second electrophoresis buffer than in the first electrophoresis buffer. The second electrophoresis buffer, when used in the apparatus of present invention, also needs to have a higher density compared to the density of the first electrophoresis buffer. That is important to prevent, or at least reduce, significant mixing of the two buffers and to keep the second buffer in the conduit during electroelution. The density may be sufficiently higher due only to the higher concentration of ions in the second electrophoresis buffer. When that is not the case, then a non-charged small molecular weight compound, or a polymer, can be added to the buffer to increase its density. Suitable compounds include, for example, sucrose and glycerol, while suitable polymers include dextran and Ficoll. The optimal composition of the second electrophoresis buffer depends on the composition and concentration of the first electrophoresis buffer, on the volume of the conduit, on the expected duration of electroelution and on the subsequent processing of the electroeluted molecules that is planned. For example, when electroeluting DNA from a gel with 30 mM Tris-acetate, 0.75 mM EDTA pH of 8.1 as the first electrophoresis buffer, then the second electrophoresis buffer can be 0.6 M Tris-acetate, 15 mM EDTA pH 8.1 containing 30% (w/v) sucrose. Additional buffers are disclosed in the following Examples. It is likely that, at the end of the electroelution, the concentration of the second electrophoresis buffer will be somewhat different from the concentration of that buffer solution prior to electroelution, due to migration of ions in and out of the conduit.

Gel pieces of varying dimensions can be placed for electroelution in the apparatus of present invention. It is only necessary that the gel piece is shorter than the space between the front and back walls 10 and 11 and that the gel is completely submerged in the first electrophoresis buffer during electroelution. A typical slab gel width of about 6–20 cm, slab gel thickness of about 1–6 mm and separated zone width of about 1–10 mm determine the range of typical gel sizes that can be electroeluted according to this invention. The gel piece is placed on the bottom of the buffer compartment in the vicinity of the top opening of the conduit, so that the molecules that leave the gel migrate only a short distance through the first electrophoresis buffer. The gel piece may also be kept elevated from bottom of the buffer compartment. It may, but it does not have to, come in contact with the surface of the central block 20. In principle, the gel can be placed in either the first or the second compartments 21 and 22 respectively, that is, at either side of the conduit. However, only one side will be the correct one for a given molecule and buffer, as is known to those skilled in the art. When electroeluting negatively charged molecules, for example nucleic acids at pH 8, then the gel piece needs to be placed in the cathode buffer compartment, so that the nucleic acids must migrate to the conduit, and therefore toward the anode, when they leave the gel (FIG. 2 and FIG. 3).

The gel that contains molecules to be electroeluted can be composed of various materials. Thus, agarose gels are commonly used for separating nucleic acids and less frequently for separating proteins. Polyacrylamide gels are used for separating both nucleic acids and proteins. Novel gel materials, as disclosed for example in U.S. Pat. Nos. 5,185,466, 5,202,007 and 5,541,255, are also useful for electrophoretic separation of nucleic acids and proteins. In particular, the gels of enhanced selectivity disclosed in U.S. Pat. No. 5,840,877 and sold under trade name Spreadex provide a higher resolving power compared to any other gels, making them especially well suited for preparative electrophoresis of nucleic acids.

The gel piece tends to change its position during electroelution if not kept in place. Keeping it in the correct position can be done is several ways. One way, for example, is by contacting the gel with a few pieces of glass rod disposed on the gel side opposite to the conduit. It is preferable to use a plastic device shown in FIG. 4 for keeping the gel piece immobile. The device also helps to position the gel piece close to the conduit. When the gel slab used for separating the desired molecules is thin, then, for electroelution, it is possible to place two, or more, gel pieces one on top of the other. This allows simultaneous electroelution of the molecules separated on several gel slabs. Thin gel slabs are commonly used for electrophoresis in vertical and flat-bed mode.

While the apparatus of present invention is intended primarily for electroeluting one molecular species at a time, it is possible to construct a modified apparatus that allows simultaneous electroelution of several molecular species simultaneously, each from a different gel piece. For this purpose, divisions can be constructed in the conduit thereby dividing it into several sections, with each section collecting a different molecular species.

For operation, the apparatus of present invention needs to be connected to a direct current power supply. In the prior art, different ways of establishing this connection and constructing the power supply are well known. As the required voltage and current are high enough to represent a health hazard, safety considerations are important. Thus, power should be applied to the electrodes only when the lid of the apparatus is closed. It can be provided that opening the lid disconnects the power. The power supply may be an integral part of the apparatus, as disclosed for example in U.S. Pat. No. 6,451,192. The power supply may have a timer allowing the electroelution to run for a preset time.

Optimal time of electroelution depends on the effective charge of the molecules, oil gel concentration, on gel thickness, on the electric field strength and on the first and second electrophoresis buffer. A typical time period for electroelution will be from about 15 min to 1 hour. Following electroelution, one can stain the gel piece to check whether the electroelution was complete, and accordingly make adjustments in the electroelution time of subsequent runs, if needed. It is possible to use a light source and an optical detection means for measuring the signal coming from the molecules as they leave the gel piece. Then electroelution can be stopped once that signal decreases to a selected low value. Such a detection means together with a valve mentioned above would allow automation of the electroelution process using the apparatus of present invention.

The electrophoretic separation of molecules that will be purified can be carried out under a variety of conditions, depending on the particular molecule, its quantity and desired purity. For example, oligonucleotides (oligos) are conventionally electrophoresed on a polyacrylamide gel under denaturing conditions, with urea or formamide present in the gel. The gel is cast between two glass plates and run at elevated temperature (about 50–60° C.). The denaturant present in the gel and the elevated temperature are considered necessary for achieving adequate separation of the desired oligo from the synthesis byproducts. After electrophoresis, the bands are visualized, usually by "UV-shadowing", as known to those skilled in the art. The selected gel area is cut out and the oligo recovered, usually by crushing the gel into small particles and allowing the oligo to diffuse into a buffer in which the gel particles are incubated.

Figure 5:
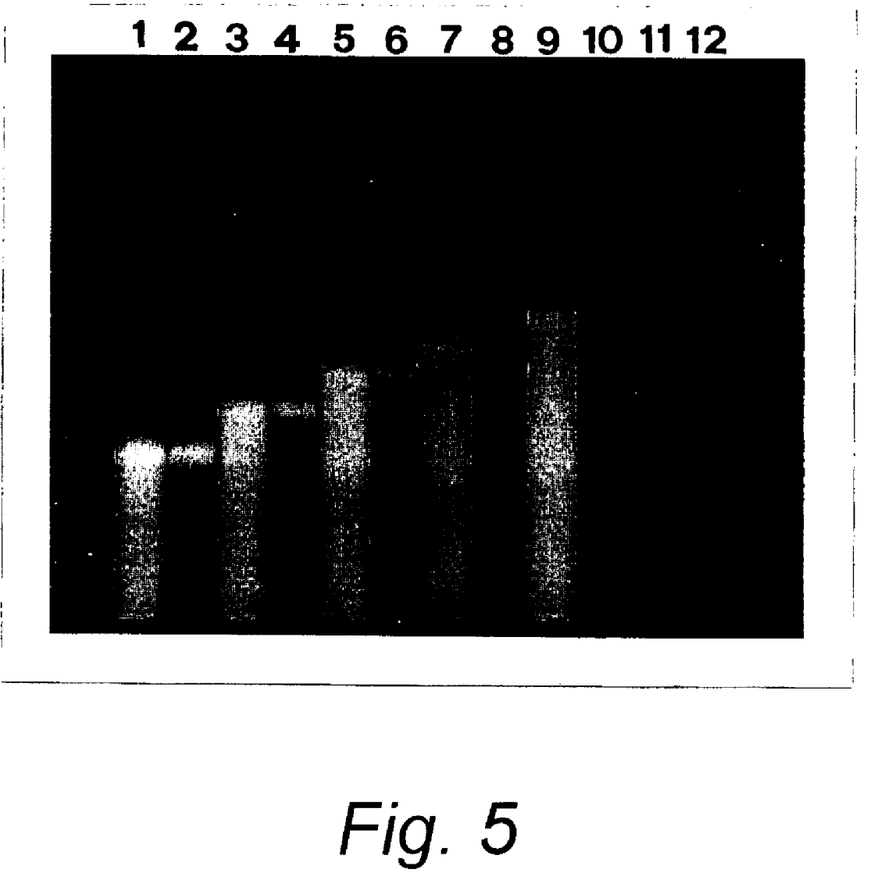
FIG. 5 depicts a gel containing long oligonucleotides of different lengths, from 80 to 130 base pairs, before and after preparative electrophoresis.

FIG. 5 shows that, under non-denaturing conditions on a Spreadex gel, 80–130 bases long oligos were separated according to their size (Example 1). Moreover, at the elevated temperatures the presence of ethidium bromide in the running buffer did not appear to cause broadening of the oligo bands. The presence of ethidium makes subsequent visualization of the bands immediately after electrophoresis convenient. No post-electrophoresis staining is necessary. Thus, in contrast to the conventional method in which the oligos are separated under denaturing conditions without a dye present during electrophoresis, here the separation was done under non-denaturing conditions in the presence of a dye. Visual detection of a dye-stained band is more sensitive than "UV-shadowing", making the precise cutting of the desired gel area simpler. The ethidium bromide stained bands were visualized and cut under blue light using a Dark Reader transilluminator (Clare Chemical Research, U.S. Pat. No. 6,198,107). When using the blue light, there is no danger of damaging the DNA or suffering skin burns, both of which may happen when using UV light. It was found that higher recovery yields were obtained when gel cutting was done under the blue light as opposed to 312 nm UV light. In one experiment, a short exposure of the stained gel to 254 nm UV light for photography significantly reduced recovery yield even though subsequent gel cutting was performed under the blue light.

After electroelution in the apparatus of present invention, the oligo is collected dissolved in a buffer of high concentration, which is not ideal for certain applications. Moreover, the concentration of the oligo is rather low when collected in about 5 ml of the second electrophoresis buffer solution. Exchanging the high concentration buffer for another one and concentrating the oligo can be achieved by several methods, including dialysis followed by water evaporation, ultrafiltration, gel filtration followed by evaporation, ion exchange chromatography, and solid phase extraction based on an ion-pairing mechanism. The last two methods allow buffer exchange and concentration to be achieved in a short time, but they require that the buffer in which the oligo is electroeluted be compatible with its binding to the solid phase. If the electroelution buffer needed to be exchanged for a binding buffer, solid phase extraction would offer little advantage over other methods. Now, it was found that a high concentration (0.5–1.0 M) buffer containing triethylamine and acetic acid pH 8, that is suitable as the second electrophoresis buffer, represents also a suitable buffer for binding to a solid phase. Conventionally, ion pairing chromatography is carried out using buffers of a significantly lower concentration, about 0.1 M (Gilar and Bouvier, Journal of Chromatography, 2000, 890:167–177). Two solid phases were found adequate, including one composed of poly (divinylbenzene-N-vinylpyrrolidone) produced by Waters (sold under trade name Oasis HLB) and the other composed of C-18 silica (end capped, Fluka). The oligos could be bound to these solid phases in a high concentration second electrophoresis buffer and, after washing, eluted with acetonitrile in a low volume, as described in Example 1 and 2. Example 3 describes preparative electrophoresis of a protein, bovine serum albumin.

EXAMPLES

Example 1

Preparative Electrophoresis of Long Oligonucleotides

Synthetic oligonucleotides of 80, 90, 100, 110, 120 and 130 bases were separated on Spreadex EL 300 S-2 gels (Elchrom Scientific). The gels were 9.2 cm long and covalently bound to a plastic backing. Each gel half contained one sample well that was about 12 cm long, 1.5 mm wide and 2.7 mm deep. The concentration of each oligonucleotide was estimated by measuring its absorbance at 260 nm. Between 20 and 67 OD (optical density) units of each oligo were loaded in 0.2 ml volume onto the gel. The oligo solution for loading contained 15–20% sucrose and 30–60 mM Tris-acetate-EDTA (TAE) buffer. Prior to electrophoresis, the gels were temperature equilibrated by placing them inside the SEA 2000 electrophoresis apparatus (Elchrom Scientific) on a plastic frame (Catamaran) for about 20 min.

Electrophoresis was carried out for 90 min at an electric field strength of 10 V/cm, at elevated temperatures using 30 mM TAE as the running buffer. The 80-mer and 100-mer were run at 55° C., the 110-mer and 120-mer at 60° C. and the 90-mer at 65° C. The running buffer contained 0.2 µg/ml of ethidium bromide. The gels contained no ethidium bromide. During electrophoresis ethidium ion enters the gel, migrating in the direction opposite to DNA.

After electrophoresis, each gel was briefly rinsed twice with deionized water. Then it was transferred to a blue light transilluminator (Dark Reader, Clare Chemical Research), with the gel plastic backing facing down. The position of the major band was visualized and a sharp needle was used to cut a line just above and just below the major band. Then, using a nylon string, the gel was released from the backing, up to the two lines cut with the needle. The lower part of the gel, below the major band, was discarded. The gel piece, in the form of a strip about 12 cm long, 2–3 mm wide and 3 mm thick, was transferred to the apparatus of present invention.

Figure 4:
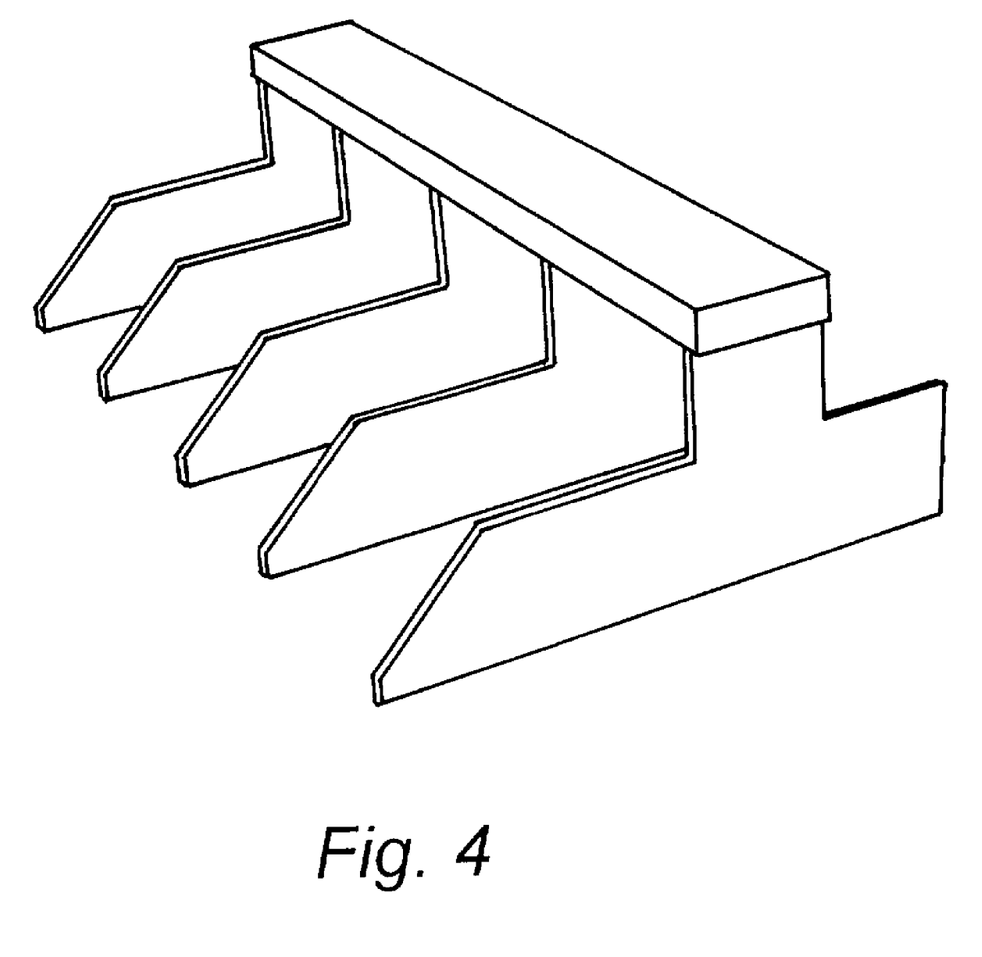
FIG. 4 is a perspective view of a means for fixing the gel in place.

Before transfer, the apparatus was prepared in the following way:

About 5 ml of a 1 M triethylammonium acetate buffer pH 8 containing 30% sucrose was withdrawn into a 10 ml plastic disposable syringe. The syringe was attached to a tubing connected to the opening at the bottom of the conduit. The piston of the syringe was pushed slightly to fill all the tubing with the buffer. Then, about 250 ml of 30 mM Tris-acetate-0.75 mM EDTA buffer pH 8.1 was poured into the apparatus of present invention. The cut gel piece was placed in the cathode compartment and positioned close to the opening of the conduit using a plastic frame (FIG. 4).

After placing the gel strip in correct position, the conduit was filled with the 1 M triethylammonium acetate buffer by slowly pushing the piston of the syringe. The lid of the apparatus was closed, and the power applied (200 V). The current was about 80 mA and it increased with time. The electroelution was carried out for 30 min. Then the power was switched off, and about 5.5 ml of buffer was withdrawn into the syringe. The syringe was disconnected from the tubing over a sink and the electrophoresis buffer was drained from the apparatus. The apparatus was immediately rinsed with deionized water.

To concentrate the electroeluted oligo, and to remove the buffer ions and sucrose, the oligo was adsorbed to a solid phase composed of polyvinylpyrrolidone-divinylbenzene particles packed in a column (Oasis HLB Vac cartridge, 60 mg, Waters). The column was first washed with 1 ml acetonitrile and then with 1 ml of 0.1 M triethylammonium acetate buffer pH 8. The flow rate was adjusted such that it took about 15–20 min to pass the whole 5.5 ml volume over the column. The column was then washed with 2 ml of 0.1 M triethylammonium acetate buffer followed by 2 ml of deionized water. The oligo was eluted with 0.5 ml of 80% acetonitrile in deionized water. The concentration of the purified oligo was determined by absorbance measurement at 260 nm. The yield of purified oligos varied from 2.1 to 9.7% (Table 1).

TABLE 1

| Oligo size (bases) | Run Temperature (° C.) | Amount Loaded (OD) | Recovery Yield (OD) |
|---|---|---|---|
| 80 | 55 | 67.2 | 3.2 (4.8%) |
| 90 | 65 | 55.5 | 2.2 (4.0%) |
| 100 | 55 | 54.9 | 1.9 (3.5%) |
| 110 | 60 | 43.1 | 0.9 (2.1%) |
| 120 | 60 | 59.4 | 2.4 (4.0%) |
| 130 | 60 | 20.7 | 2.0 (9.7%) |

The purity of the oligos was checked by running the starting oligos and purified oligos (FIG. 5) in adjacent electrophoresis lanes. The gel was Spreadex EL 300 S-26 run at 10 V/cm for 90 min at 60° C. The gel was stained with SYBR Gold (Molecular Probes). As can be seen, all starting oligos contained a lot of synthesis byproducts that had migration rates higher and lower than the migration rate of the desired oligo that is visible as a major band. After preparative electrophoresis according to present invention, all oligos showed a high degree of purity (FIG. 5). The relatively low recovery yields based on absorbance measurements (Table 1) are not surprising in view of the low amount of the desired oligo in the starting material. If needed, it is possible to subject an oligo to a second preparative electrophoresis to further increase its purity.

Example 2

Preparative Electrophoresis of Short Oligos

Figure 6:
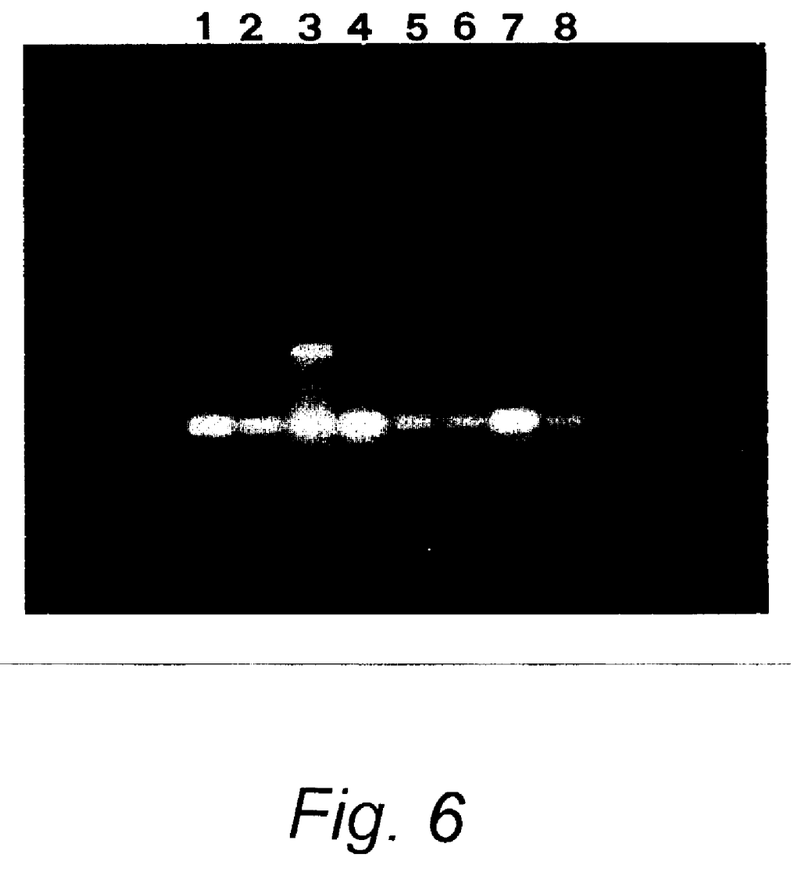
FIG. 6 depicts a gel containing short oligonucleotides before and after preparative electrophoresis

Two oligonucleotides, a 22-mer and a 25-mer, were synthesized at two different custom oligo synthesis companies at 1 μmole scale. One pair was purified by reverse phase chromatography while the other pair was just desalted by the respective manufacturer. The whole amounts of the received oligos (ranging from 32 to 98 OD) were dissolved in 0.2 ml of loading buffer (60 mM TAE containing 30% sucrose) and loaded to one half of a Spreadex EL 300 S-2 gel (Elchrom Scientific). The gels were run at 55° C. for 50 min at 10 V/cm with 0.2 μg/ml of ethidium bromide in the running buffer. Following visualization, gel cutting, electroelution, binding to solid phase and elution as described in Example 1, the starting and purified oligos were analyzed on a Spreadex EL 300 S-26 gel (10 V/cm, 50 min, 55° C.). The gel was stained after electrophoresis with SYBR Gold. FIG. 6 shows the result, where lanes 1, 3, 5 and 7 show the starting oligos and lanes 2, 4, 6, and 8 are the oligos purified by preparative electrophoresis. Lanes 1 and 3 contained oligos that were reverse phase purified by the manufacturer. While the starting oligo in lane 1 is of a good purity, showing only a minor impurity band above the major band (which impurity was removed after preparative electrophoresis, lane 2), the second oligo contained close to 50% of an impurity visible as a strong band migrating above the expected oligo band (lane 3). That impurity was completely eliminated by preparative electrophoresis (lane 4). When the concentration of an oligo is determined by UV measurement, for example in order to prepare a primer mix containing both primers at identical concentration for PCR, then the presence of the impurity seen in lane 3 makes such concentration adjustment incorrect. After preparative electrophoresis, the UV measurement allows precise determination of oligo concentration. Also the other pair of oligos, just desalted after synthesis, showed improved purity after preparative electrophoresis (lanes 5 and 7 versus lanes 6 and 8). Recovery yields were 34% (oligo in lane 2), 6% (lane 4), 32% (lane 6) and 22% (lane 8). The gel with the oligo run in lane 3 was exposed to 254 nm UV light for photography prior to cutting the band of interest under blue light.

Several short oligonucleotides (20–35 bases) synthesized at 0.2 μmole scale were purified using the same procedure, with typical recovery yield of about 30–35%. In another experiment, the oligo was bound in the electroelution buffer (0.5 M) to C-18 silica (100 Å, end capped, Fluka) column, containing 100 mg of the solid phase. Elution with 80% acetonitrile in water yielded about 30% of the purified oligo. The flow rate through the silica column was lower that when using Oasis HLB column.

Example 3

Bovine serum albumin (BSA, 100 mg, purchased from Serva) was dissolved in 0.95 ml of 30 mM Tris-acetate-EDTA (TAE) buffer pH 8.1. An aliquot of 0.25 ml was mixed with 0.25 ml of a loading buffer containing 30% sucrose in the same TAE buffer. Based on 280 nm absorbance measurement, 5.96 OD units of the protein were loaded in 0.2 ml to a Clearose BG S-2 gel (Elchrom Scientific). The gel was run at 10 V/cm for 35 min at 20° C. Then the gel was briefly rinsed twice with deionized water, followed by 5 min incubation in a 0.2 M solution of immidazol in water. The gel was quickly rinsed with water and then incubated for 2–3 min in 0.3 M solution of zinc chloride. This procedure resulted in negative staining of protein bands (Fernandez-Patron et al., Biotechniques, 1992, 4: 564–573). The protein zone (about 9 mm wide) was cut and transferred to the apparatus of present invention, without any additional treatment. The first electrophoresis buffer (250 ml) was 30 mM TAE and the second electrophoresis buffer (5 ml) was 0.6 M TAE containing 30% sucrose. Electroelution was carried out at 200 V for 30 min, with cold water poured into cavity of the central block prior to turning on the power. The collected protein was extensively dialyzed, twice for about 12 h against 1 l of 30 mM TAE. Based on 280 nm absorbance measurement, 2.0 OD of the protein was recovered (yield 33.5%).

While the present invention has been described in considerable detail, it will be apparent to those skilled in the art that modifications can be made in design and procedures without departing from the spirit of the invention as defined by the appended claims.

What is claimed is:

1. An apparatus for carrying out electroelution of target molecules from a gel containing said molecules comprising:
    two spaced apart electrode compartments, each of which comprises side wall(s) and a bottom at least one electrode and is adapted to hold a liquid therein, and a conduit disposed between and in communication with both of said electrode compartments and adapted to hold a liquid therein,
    wherein said electrode compartments are each adapted to hold a first electrophoresis buffer solution therein
    wherein said conduit is adapted to hold a second electrophoresis solution in effective contact with said first electrophoresis buffer solution; and
    wherein, when said electrode compartments are disposed substantially horizontally, at least a major portion of the conduit is disposed at a level below the level of the bottom of said electrode compartments proximal to the conduit,
    wherein said apparatus is adapted to have a gel specimen containing molecules of interest disposed in said first electrophoresis buffer solution proximate to a confluence of one of said electrode compartments and said conduit, and
    wherein said electrophoresis solutions are adapted to permit an electrical current, sufficient to cause electroelution of molecules of interest from said gel and to cause such electroeluted molecules to be transferred into said second electrophoresis solution.

2. An apparatus as claimed in claim 1 wherein said conduit is disposed wholly below the level of the bottom of said electrode compartments proximal to said conduit.

3. An apparatus as claimed in claim 2 wherein the bottoms of both of said electrode compartments are in a substantially common plane.

4. An apparatus as claimed in claim 2 wherein said conduit is substantially symmetrically disposed between said electrode compartments.

5. An apparatus as claimed in claim 1 further comprising a blocking member disposed between said electrode compartments so as to form said conduit at least partially below the bottom of said electrode compartments; wherein said blocking member effectively separates the first electrophoresis buffer in each electrode compartment, respectively, from each other.

6. An apparatus as claimed in claim 5 further comprising heat exchange means operatively associated with said blocking member.

7. An apparatus as claimed in claim 5 wherein said conduit is "V" shaped.

8. An apparatus as claimed in claim 5 wherein said conduit is "U" shaped.

9. An apparatus as claimed in claim 5 wherein said conduit is narrower than the depth of said first buffer solution and is operatively joined to said compartment through an area that is wider that the width of the conduit.

10. An apparatus as claimed in claim 1 wherein said bottom comprises a first surface spaced from said conduit and at least one second surface; wherein said surfaces are vertically spaced from each other.

11. An apparatus as claimed in claim 10 wherein said first surface is proximate to at least one of said electrode.

12. An apparatus as claimed in claim 1 further comprising a lid.

13. An apparatus as claimed in claim 12 wherein said lid comprises an electrical switch disposed between a power source and at least one of said electrodes; wherein said switch is adapted to be closed by applying said lid to said apparatus and is adapted to be opened by removing said lid from said apparatus.

14. An apparatus as claimed in claim 1 further comprising at least one electrode in each of said compartments adapted to be in operative relationship to said first electrophoresis buffer solution; and wherein, when said bottom is in a substantially horizontal plane, the depth of said first buffer solution is greater proximate to at least one of said electrodes than it is proximate to said conduit.

15. An apparatus as claimed in claim 14 wherein each of said electrodes comprises two separate wires.

16. An apparatus as claimed in claim 1 wherein said conduit is transversely divided into at least two separate zones.

17. An apparatus as claimed in claim 1 further comprising a means to fix said gel specimen in place on said bottom during electroelution.

18. An apparatus as claimed in claim 1 wherein all of the structural elements, except the electrodes, comprise insulating material.

19. An apparatus as claimed in claim 1 further comprising means to introduce and to extract said second buffer solution at the lowest point of said conduit.

20. A method of electroelution of molecules from a gel specimen comprising:
    providing a lower density, first buffer solution, containing a lower concentration of buffer ions, in a first reservoir;
    providing a higher density, second buffer solution, containing a higher concentration of buffer ions, in a second reservoir disposed below the bottom of the first reservoir and in operative communication with said first reservoir,
    maintaining said first and second buffer solutions in effective contact with each other and preventing substantial mixing of said first and second buffer solutions;
    disposing a gel specimen, containing target molecules, in said first reservoir covered by said first buffer solution and disposed proximate to the confluence of said first and second reservoirs;

passing a DC current through said first and second buffer solutions in an amount and for a time sufficient to elute target molecules from said gel specimen and cause said eluted target molecules to pass into said second buffer solution and recovering said second buffer solution containing said eluted target molecules.

21. A method as claimed in claim 20 further comprising:

subjecting a mixture of nucleic acid molecules to submerged gel electrophoresis, operated under non-denaturing conditions at a temperature of up to about 70° C., in the presence of an electrophoresis gel and an electrophoresis buffer solution containing ethidium bromide, whereby separating said nucleic acid molecules detecting ethidium stained nucleic acids by visualizing the gel, containing said molecules, under illumination;

selecting a gel piece containing a nucleic acid band of interest; and subjecting said selected gel piece to said electroelution.

22. A method as claimed in claim 20 further comprising: visualizing said stained gel with blue light.

* * * * *